United States Patent
Gregory et al.

(10) Patent No.: US 8,582,843 B2
(45) Date of Patent: Nov. 12, 2013

(54) MORPHOMETRY OF THE HUMAN KNEE JOINT AND PREDICTION FOR OSTEOARTHRITIS

(75) Inventors: Jennifer Susan Gregory, Aberdeen (GB); Richard Malcom Aspden, Ellon (GB); Rebecca Jane Barr, Angus (GB); Kanako Yoshida, Aberdeen (GB); David Macaulay Reid, Aberdeen (GB)

(73) Assignees: Wyeth Pharmaceuticals, Inc. NJ (US); TMRI, Ltd. (GB)

( * ) Notice: Subject to any disclaimer, the term of this patent is extended or adjusted under 35 U.S.C. 154(b) by 208 days.

(21) Appl. No.: 13/058,615

(22) PCT Filed: Aug. 12, 2009

(86) PCT No.: PCT/GB2009/051012
§ 371 (c)(1),
(2), (4) Date: Jun. 24, 2011

(87) PCT Pub. No.: WO2010/018407
PCT Pub. Date: Feb. 18, 2010

(65) Prior Publication Data
US 2011/0257507 A1    Oct. 20, 2011

(30) Foreign Application Priority Data

Aug. 12, 2008   (GB) .................................. 0814714.2
May 8, 2009    (GB) .................................. 0907932.8

(51) Int. Cl.
*G06K 9/00*    (2006.01)
*A61B 5/05*    (2006.01)

(52) U.S. Cl.
USPC .......................................... 382/128; 600/410

(58) Field of Classification Search
USPC .......... 382/128–134; 600/407, 410, 411, 425, 600/427; 606/88, 90; 623/18.11, 19.11, 623/19.12, 20.12, 20.14, 20.24, 39
See application file for complete search history.

(56) References Cited

U.S. PATENT DOCUMENTS

| 5,259,384 A | 11/1993 | Kaufman et al. |
| 5,348,009 A | 9/1994 | Ohtomo et al. |

(Continued)

FOREIGN PATENT DOCUMENTS

| EP | 0570936 | 9/2000 |
| WO | 94/06351 | 3/1994 |

(Continued)

OTHER PUBLICATIONS

Practical Statistics for Medical Research, pp. 1-99.

(Continued)

*Primary Examiner* — Abolfazl Tabatabai
(74) *Attorney, Agent, or Firm* — Renner Kenner Greive Bobak Taylor & Weber (57) ABSTRACT

Apparatus and method for analyzing the morphometry of a human knee joint. The apparatus comprises:
   image receiving means for receiving a digital image of a knee joint;
   image analysis means comprising an Active Shape Model (ASM) configured to identify a set of landmark points on said image, wherein said set of landmark points includes points which define regions of the knee formed by the femur and the tibia, the ASM being further configured to generate an image data-set from the co-ordinates of said landmark points; and
   data comparison means for comparing said image data-set with one or more comparative data-sets to thereby obtain value(s) for one or more output modes which characterize the variation of the image data-set from the comparative data-set(s), to thereby provide an indication of the presence and/or severity of osteoarthritis in the knee and/or the risk of the knee joint developing osteoarthritis.

14 Claims, 8 Drawing Sheets

(56) References Cited

U.S. PATENT DOCUMENTS

| | | | |
|---|---|---|---|
| 5,649,929 A * | 7/1997 | Callaway | 606/88 |
| 5,931,780 A | 8/1999 | Doi et al. | |
| 6,038,281 A * | 3/2000 | Mazess | 378/54 |
| 6,213,958 B1 | 4/2001 | Winder | |
| 7,379,529 B2 | 5/2008 | Lang | |
| 7,660,453 B2 | 2/2010 | Lang | |
| 7,760,923 B2 * | 7/2010 | Walker et al. | 382/128 |
| 7,769,213 B2 | 8/2010 | Gregory et al. | |
| 7,929,745 B2 * | 4/2011 | Walker et al. | 382/128 |
| 2004/0101186 A1* | 5/2004 | Tong et al. | 382/132 |
| 2004/0242987 A1 | 12/2004 | Liew et al. | |
| 2005/0010106 A1 | 1/2005 | Lang et al. | |

FOREIGN PATENT DOCUMENTS

| | | |
|---|---|---|
| WO | 0138824 | 5/2001 |
| WO | 2005045730 | 5/2005 |
| WO | 2006104707 | 10/2006 |
| WO | 2007058918 | 5/2007 |

OTHER PUBLICATIONS

Practical Statistics for Medical Research, pp. 100-199.
Practical Statistics for Medical Research, pp. 200-299.
Practical Statistics for Medical Research, pp. 300-399.
Practical Statistics for Medical Research, pp. 400-499.
Practical Statistics for Medical Research, pp. 500-611.
Assessment of osteoporosis and osteoarthritis using active shape and active apperance models with DXA scans; Gregory J.S, Barr R.J, Stewart A, Reid D.M, Aspden R.M; Jul. 2007; Journal of Bone and Mineral Research, vol. 22, No. 7.
Fracture risk assessment model: Do values derived from Western populations apply to other Caucasians?; Arabi A, Awada H, Baddoura R, Haddad S, Khoury N.J, Ayoub G, Fuleihan G. El-hail; Sep. 2005; Journal of Bone and Mineral Research; vol. 20, No. 9, Suppl.
Femoral Fracture Risk assessment after intensity modulated radiation therapy (IMRT) for the treatment of soft tissue sarcoma using a novel mathematical model; Song Y, Wang S, Chan M, Chandra B, Dhawan A, Song Y; 2006; IEEE cat. No. 06CH37748.
Measurement of femoral Neck anteversion in 3D. 2. 3D modelling method; Kim J.S, Park T.S, Park S.B, Kim J.S, Kim I.Y, Kim S.I; Nov. 2000; Medical & Biological Engineering & Computing; vol. 38 No. 6.
Automatic reconstruction of patient-spefic surface model of a proximal femur from calibrated X-ray images via Bayesian Filters; Guoyan Zheng, Xiao Dong; 2007; Advanced Intelligent Computing Theories and Applications. With Aspects of Theoretical and Methodological Issues. Proceedings Third International Conference on Intelligent Computing, ICIC; vol. 4681.
Femur bone mass distribution by DXA predicts hip fracture risk better than femur bone density; Del Rio L, Di Gergorio S, Bagur A, et al; Jan. 2006; Calcifield Tissue International; vol. 78, Supp. 1.
DXA and active appearance modelling: A novel method for assessment of Osteoarthritis; Gregory J.S, Campbell CD, Yoshida K, et al; Jun. 2007; Bone (New York); vol. 40, No. 6 Supp 2.
Use of DXA-Based Structural engineering models of the proximal femur to predict hip fracture; Yan L, Peel N, Clowes J, McCloskey E.V, Eastell R; Sep. 2007; Journal of Bone and Mineral Research; vol. 22, supp 1.
A DXA-based composite beam model of the proximal femur for stress estimation; Yang L, McCloskey E.V, Eastell R; Jul. 2006; Journal of Bone and Mineral Research; vol. 21, No. 7.
Does follow-up duration influence the ultrasound and DXA prediction of hip fracture? The EPIDOS prospective study; Hans D, Schott A.M, Duboeuf F, Durosier C, et al; Aug. 2004; Bone (New York); vol. 35, No. 2.
Assessment of fracture risk by bone density measurements; Jergas M, Glesser C.C; Jul. 1997; Semin Nucl Med; vol. 27, No. 3.
Femoral strength is better predicted by finite element models than QCT and DXA; Cody D.D, Gross G.J, Hou F.J, et al; Oct. 1999; Journal of Biomechanics; vol. 32, No. 10.
A mathematical model that improves the validity of osteoarthritis diagnoses obtained from a computerized diagnostic database; Gabriel S.E, Crowson C.S, O'Fallon W.M; Sep. 1996; Journal of Clinical Epidemiology; vol. 49, No. 9.
Biomedical evaluation of hip fracture using finite element model that models individual differences of femur; Harada Atsushi, Mizuno Masashi, Nakanishi Takafumi, et al; Sep. 2004; Nippon Kikai Gakki Ronbunshu A; vol. 70, No. 9.
3D reconstruction of femoral shape using a parametric model and two 2D fluoroscopic images; Kurazume R, Nakamura K, Okada T, Sato Y, et al; 2007; 2007 IEEE International Conference on Robotics and Automation; IEEE Cat No. 07CH37836D.
Analysis of ultrasound images based on local statistics, application to the diagnosis of development dysplasia of the hip; de Luis-Garcia R, Aja-Fernandez S, Cardenes-Almeida R, et al; 2007; 2007 IEEE Ultrasonics Symposium.
Subject-specific finite element models implementing a maximum principal strain criterion are able to estimate failure risk and fracture location on human femurs tested in vitro; Schileo E, Taddei F, Cristofolini L, Viceconti M; 2008; Journal of Biomechanics; vol. 41, No. 2.
Wave proppagation characteristics in long bones to diagnose osteoporosis; Chen I.I.H, Saha S; 1987; Journal of Biomechanics; vol. 20, No. 5.
Reconstruction of patient-specific 3D bone model from biplanar X-ray images and point distribution models; Zheng G; 2006 International Conference on Image Processing.
Early identification of radiographic osteoarthritis of the hip using an active shape model to quantify changes in bone morphometric features: can hip shape tell us anything about the progression of osteoarthritis?; Gregory JS, Waarsing JH, Day J, Pols HA, Reijman M, Weinans H, et al; Nov. 2007; Arthritis Rheum; 56(11).
Altman, R.D. & Gold, G.E. 2007, "Atlas of individual radiographic features in osteoarthritis, revised", Osteoarthritis and Cartilage, vol. 15, No. SU PP L. 1, pp. 1-56.
Arthritis Research Campaign. Arthritis: the big picture. 2002. Cheltenham, Arthritis Research Campaign.
Deletion of active ADAMTS5 prevents cartilage degradation in a murine model of osteoarthritis; Glasson SS, Askew R, Sheppard B, Carito B, Blanchet T, Ma HL et al; Nature 434: 644-648, 2005.
Magnetic resonance imaging (MRI) of articular cartilage in knee osteoarthritis (OA): morphological assessment; Eckstein F, Clouttini F, Raynauld JP, Waterton JC, Peterfy C; Osteoarthritis Cartilage 14 Suppl A: A46-A 75, 2006.
A method for assessment of the shape of the proximal femur and its relationship to osteoporotic hip fracture; Gregory JS, Testi D, Stewart A, Undrill PE, Reid DM, Aspden RM; Osteoporos Int 15: 11, 2004.
Bone shape, structure and density as determinants of osteoporotic hip fracture: A pilot study investigating the combination of risk factors; Gregory JS, Stewart A, Undrill PE, Reid DM, Aspden RM; Invest Radiol 40: 591-597, 2005.
Osteoarthritis: a problem of growth not decay?; Aspden RM; Rheumatology 47: 1452-1460, 2008.
Osteoarthritis is a systemic disorder involving stromal cell differentiation and lipid metabolism; Aspden RM, Scheven BAA, Hutchison JD; Lancet 357: 1118-1120,2001.
High levels of fat and (n-6) fatty acids in cancellous bone in osteoarthritis; Plumb MS, Aspden RM; Lipids in Health and Disease 3: 12, 2004.
The association of lipid abnormalities with tissue pathology in human osteoarthritic articular cartilage; Lippiello L, Walsh T, Fienhold M; Metabolism 40:571-576, 1991.
Bone marrow fat in osteoarthritis assessed using Magnetic Resonance Imaging; Ahearn TS, Gregory JS, Redpath TW, Semple SIK, Hutchison JD, Knight DJ et al; Arthritis Res Ther submitted 2008.
Development of a logically derived line drawing atlas for grading knee osteoarthritis; Nagaosa Y, Mateus M, Hassan B, Lanyon P, Doherty M; Annals of the Rheumatic Diseases 59: 587-595, 2000.
Whole-organ magnetic resonance imaging score (WORMS) of the knee in osteoarthritis; Peterfy, C. G., Guermazi, A., Zaim, S., Tirman, P. F. J., Miaux, Y., White, D., et al.; 2004; Osteoarthritis and Cartilage, 12(3), 177-190.

(56) References Cited

OTHER PUBLICATIONS

"Substantial superiority of semiflexed (MTP) views in knee osteoarthritis: A comparative radiographic study, without fluoroscopy, of standing extended, semiflexed (MTP), and schuss views"; Buckland-Wright, J.C., Wolfe, F., Ward, R.J., Flowers, N. & Hayne, C; 1999; Journal of Rheumatology, vol. 26, No. 12, pp. 2664-2674.
Council for International Organizations of Medical Sciences & University of Manchester. Dept. Rheumatology 1963, The epidemiology of chronic rheumatism: a symposium organized by the Council for International Organizations of Medical Sciences . . . ; Kellgren, J.H. proceedings held Aug. 28 to Sep. 1, 1961 J, Blackwell Scientific Publications, Oxford.
Practical statistics for medical research, 1 st edn, Chapman and Hall, London; Altrman, D.G; 1991; New York.
"Bone marrow edema in the knee in osteoarthrosis and association with total knee arthroplasty within a three-year follow-up"; Scher, C, Craig, J. & Nelson, F.; 2008; Skeletal Radiology, vol. 37, No. 7, pp. 609-617.
Fractal analysis of trabecular bone in knee osteoarthritis (OA) is a more sensitive marker of disease status than bone mineral density (BMD); Messent EA, Buckland-Wright JC, Blake GM; 2005; Calcified Tissue International, 76 (6), pp. 419-425.
Comparison of histomorphometric descriptions of bone architecture with dual-energy X-ray absorptiometry for assessing bone loss in the orchidectomized rat; Libouban H, Moreau MF, Legrand E, Audran M, Basle MF, Chappard D; 2002; Osteoporosis International ; 13 (5), pp. 422-428.
Computed tomography image analysis of the calcaneus in male osteoporosis; Cortet B, Dubois P, Boutry N, Palos G, Cotten A, Marchandise X; 2002; Osteoporosis International; 13 (1), pp. 33-41.
Bone microarchitecture and bone fragility in men: DXA and histomorphometry in humans and in the orchidectomized rat model; Audran M, Chappard D, Legrand E, Libouban H, Basle MF; 2001; Calcified Tissue International, 69 (4), pp. 214-217.
Diagnostic agreement of combined radiogrammetric analysis with texture analysis in the evaluation of bone density: A comparison with dual energy X-ray absorptiometry; Trivitayaratana W, Trivitayaratana P; 2001; Journal of the Medical Association of Thailand, 84 (suppl. 2), pp. S599-S604.
Texture analysis of X-ray radiographs is more reliable descriptor of bone loss than mineral content in a rat model of localized disuse induced by the *Clostridium botulinum* toxin; Chappard D, Chennebault A, Moreau M, Legrand E, Audran M, Basle MF; 2001; Bone, 28 (1), pp. 72-79.
Semiautomatic Segmentation of Vertebrae in Lateral X-rays Using a Conditional Shape Model; et al; Sep. 20, 2007; Academic Radiology; vol. 14, No. 10.
International Search Report of International Patent Application No. PCT/GB2009/051011.
Written Opinion of International Patent Application No. PCT/GB2009/051011.
International Search Report of International Patent Application No. PCT/GB2009/051012.
Written Opinion of International Patent Application No. PCT/GB2009/051012.
Gregory, et al., Hip fractures, morphometry and geometry, Apr. 2002.
Testi, et al., Prediction of Hip Fracture Can Be Significantly Improved by a Single Biomedical Indicator, 2002.
J.S. Gregory, et al., "A method for assessment of the shape of the proximal femur and its relationship to osteoporotic hip fracture", International Osteoporosis Foundation and National Osteoporosis Foundation, No. 7, 2003, pp. 5-11, United Kingdom, XP-002318248.
C. Bergot et al., "Hip Fracture Risk and Proximal Femur Geometry and DXA Scans", International Osteoporosis Foundation and National Osteoporosis Foundation, 2002, pp. 542-550, United Kingdom, XP-002318249.
C.J. Taylor, "Model-based interpretation of complex and variable images", Department of Medical Biophysics, 1997, United Kingdom, XP-002318250.
J.S. Gregory et al., Analysis of Trabecular Bone Structure Using Fourier Transforms and Neural Networks:, IEEE Transaction on Information Technology in Biomedicine, vol. 3, No. 4, Dec. 1999, pp. 289-294, XP-002318251.
Sharmila Majumdar, et al., "Fractal analysis of radiographs: Assessment of trabecular bone structure and prediction of elastic modulus and strength", Magnetic Resonance Science Center and Osteopososis and Arthritis Research Group, Department of Radiology, University of California, San Francisco, California 94143, Med. Phys. 26 (7), Jul. 1999.
Slison Stewart, et al., "Bone Density and Bone Turnover in Patients with Osteoarthritis and Osteoporosis", The Journal of Rheumatology, 1999; 26:3 pp. 622-626.

\* cited by examiner

Medial        Lateral

MORPHOMETRY OF THE HUMAN KNEE JOINT AND PREDICTION FOR OSTEOARTHRITIS

The present invention relates to apparatus for predicting and monitoring osteoarthritis of the knee.

Over 0.5 million people in the UK have moderate to severe osteoarthritis of the knee, which causes considerable pain and ultimately loss of mobility in the joint, as the disease results in the breakdown of cartilage in the knee joint and thickening of the bone.

Various treatments and therapies are available which aim to manage the condition and slow its progression. Typically, however, such measures are more effective if started during the early stages of the disease.

It is therefore desirable to diagnose the condition as early as possible and, ideally, to predict those at risk of developing the disease before they begin to exhibit the symptoms.

Standard clinical assessment methods for detecting the presence of osteoarthritis include geometrical analysis of bone shape based on radiographic images taken of the patient's joint. However, such methods are relatively crude, and can only provide a reliable indication of the presence of the disease at a relatively advanced stage, which means that the effectiveness of any treatment or therapy is limited.

Moreover, the rate of progression of osteoarthritis varies greatly between individuals. It would therefore be desirable to determine the severity of the disease in terms of a predicted rate of disease progression.

Clinical imaging methods such as the Kellgren Lawrence (KL) scoring system have previously been used in research and in clinical trials for analysing the effects of osteoarthritis in various joints. Specifically, osteoarthritis in the knee has been quantified based on joint space width as measured from radiographic and MRI images of the knee. With such methods, images of the joint are analysed, and a score is assigned to features of the image such as joint space width, the presence of osteophytes and sub-chondral sclerosis.

However, such systems require a specially trained clinician to analyse the image. Moreover, such systems are inherently subjective, in that the results rely on the individual clinician's perception and analysis of the image. Accordingly, such methods do not lend themselves to use in routine clinical practice, and have not previously been used for this purpose.

As disclosed in WO 2005/045730, Active Shape Modelling techniques have been used to objectively monitor the progression of osteoporosis to predict bone fracture risk for a patient, based on Dual X-Ray Absorptiometry (DXA) images of the proximal femur. Such techniques may be used in isolation, or in combination with texture analysis of the image using Fourier transforms and Principal Component Analysis. This document also refers to the potential use of such methods for measuring the progression of osteoarthritis or Paget's disease by quantifying the deformation of the femur. However, the use of such techniques have not previously been disclosed in the context of the knee.

It is an object of the present invention to improve on the results achievable with previously known methods and apparatus.

According to one aspect of the present invention there is provided apparatus for analysing the morphometry of a human knee, the apparatus comprising:

image receiving means (an image receiving module) for receiving a digital image of a knee;

image analysis means (an image analysis module) comprising an Active Shape Model (ASM) configured to identify a set of landmark points on said image, wherein said set of landmark points includes points which define regions of the knee formed by the femur and the tibia, the ASM being further configured to generate an image data-set from the co-ordinates of said landmark points; and data comparison means (a data comparison module) for comparing said image data-set with one or more comparative data-sets to thereby obtain value(s) for one or more output modes which characterise the variation of the image data-set from the comparative data-set(s), to thereby provide an indication of the presence and/or severity of osteoarthritis in the knee and/or the risk of the knee joint developing osteoarthritis.

Although the data set generated by the ASM is dependent on the location of the landmark points on the image, this data does not describe the individual anatomical features defined by the landmark points. Rather, the data set describes patterns of features in the overall joint shape.

By including features of the femur and the tibia in the ASM, the present inventors have found that the ASM identifies patterns in the shape of these parts of the knee, which have not previously been linked with the presence or severity of OA.

The apparatus of the present invention is thus able to identify subtle variations in the overall shape of the knee, to thereby identify a risk of a patient developing osteoarthritis, or to identify the severity of the disease in terms of, for example, a predicted rate of disease progression or a predicted rate of progression to surgical intervention.

The invention thus allows for earlier and more sensitive analysis of images of a patient's knee than previously achievable, and is even able to identify healthy patients who are at risk of developing osteoarthritis in the future. In particular, the present invention has the ability to identify individuals who are most likely to develop OA before other clinical methods such as KL grade.

This enables treatment and therapy for reducing or delaying the progression of the disease to be commenced at an early stage, when it will be more effective.

The present invention is also able to provide sensitive, quantitative measures that are highly correlated with traditional clinical measures, such as KL grade, thereby avoiding the undesirable subjectivity of such measures.

Moreover, the invention can be used to predict the risk of a patient developing osteoarthritis in their knee, and/or to monitor and predict the progression of the disease, without the need for expert analysis of the image. As the need for expert analysis of the images is reduced, results can be obtained more quickly and more cost effectively than with previous methods.

The invention not only provides an imaging biomarker for identifying early stage disease and rate of progression, but may also be used as biomarker for patent stratification and monitoring OA progression in clinical trials. Clinical trials of Disease modifying Osteoarthritic Drugs (DMOADs) are estimated to take at least 10 years using previously known markers of disease, due to the scarcity of reliable markers and the consequent difficulty of identifying individuals who are at high risk of developing the disease or who have the earliest stages of the disease. DMOADS are unlikely to be effective once cartilage breakdown and changes in the bone and surrounding soft tissues are well advanced. It is thus important to identify onset of disease as early as possible. Once a DMOAD is administered, it is important to be able to compare joint changes in the treatment group with a control group over as short a time period as possible in order to assess whether the agent is effectively slowing or preventing disease progression. The previous lack of suitable markers for incidence and progression of OA means that DMOAD development is expensive and the efficacy DMOADs is difficult to establish. However, with the present invention, changes in the joint, and hence the looked-for beneficial effects of therapy, can be detected over much shorter periods of time than previously possible, and it is possible to recruit into a clinical trial those individuals best suited to test the efficacy of DMOADs, ie, those showing the earliest signs of OA (as evidenced by clinical signs such as joint pain and stiffness) and identified as having a high risk of rapid progression.

The ASM is preferably configured to identify landmark points corresponding to or defining femoral and/or tibial osteophytes in the knee region.

The ASM is preferably configured to identify landmark points corresponding to or defining any or all of the tibial plateau, femoral condyles and intercondylar notch.

Each of the above features has been found by the inventors to add to the sensitivity of the ASM in identifying previously unrecognised patterns of features that are related to the presence and/or severity of OA.

In certain embodiments, the ASM may be further configured to identify a set of regions defined by said landmark points on the image, to generate data representative of the image intensity within each said region and include said data in the image data set. In this case, the ASM may be described as an Active Appearance Model (AAM).

In this case, the digital image of the knee is preferably a Dual X-Ray Absorptiometry (DXA) image. In such images, the image intensity represents Bone Mineral Density (BMD). This enables "textural" information about the structure of the bone within the regions defined by the landmark points to be incorporated into the data set, and thus allows features such as sub-chondral sclerosis to be taken into account by the ASM.

The comparative data-set(s) may be obtained by applying the ASM to one or more images of different knee(s). In practice, the comparative data-sets may include the image data-set for the knee that is being analysed.

The comparative data sets may include data representative of the coordinates of landmark points identified in the image, and may additionally include data representative of the image intensity in regions defined by said landmark points on the image.

The comparative data-sets may be obtained from images taken for a group of subjects, which may be selected to cover the whole range from normal to abnormal knees.

The data comparison means is preferably configured to apply Principal Component Analysis to characterise the variation of the image data-set from the comparative data-sets in terms of independent modes of variation.

Where there is more than one comparative data-set, the data comparison means preferably compares the image data-set with the comparative data-sets by examining how the location of landmark points deviates from the mean co-ordinates of the comparative data-set(s).

For example, the image data-set under analysis may be compared with the comparative data-sets and "positioned" along the mode scores in terms of how many standard deviations it is from the mean of that mode for the whole group.

The image analysis means may comprise a plurality of ASMs for identifying different sets of landmark points on the image. These may include a master-ASM and one or more sub-ASMs, each sub-ASM being configured to identify a subset of the landmark points the master ASM is configured to identify. There may be a series of one or more sub-ASMs, the first being configured to identify a subset of the landmark points the master-ASM is configured to identify, and the further sub-ASM(s) each being configured to identify a subset of the landmark points identified by the previous sub-ASM in the series.

The digital image of the knee may be obtained from a radiographic image, a Dual X-ray Absorptiometry (DXA) image, a Magnetic Resonance Image (MRI), a Computed Tomography (CT) image, or an ultrasound image thereof.

In the case of a DXA image, any suitable DXA scanner may be used, as are commercially available and known in the art.

According to another aspect of the present invention there is provided a method for analysing the morphometry of a human knee, the method comprising:

obtaining a digital image of a knee joint;

applying to said image an Active Shape Model (ASM) configured to identify landmark points on said image, wherein said landmark points include point which define regions of the knee formed by the femur and the tibia, generating an image data-set from the co-ordinates of said landmark points; and comparing said image data-set with one or more comparative data-sets to thereby obtain value(s) for one or more output modes which characterise the variation of the image data-set from the comparative data-set(s).

The values for these output modes may be interpreted as an indication of the risk of the knee developing osteoarthritis and/or the severity of osteoarthritis in the knee.

According to another aspect of the present invention there is provided a computer program for analysing the morphometry of a human knee, the program comprising:

image receiving code for receiving a digital image of a knee;

image analysis code comprising Active Shape Model (ASM) code configured to identify a set of landmark points on said image, wherein said set of landmark points includes points which define regions of the knee formed by the femur and the tibia, the ASM code being further configured to generate and store an image data-set from the co-ordinates of said landmark points; and data comparison code configured to compare said image data-set with one or more comparative data-sets to thereby obtain value(s) for one or more output modes which characterise the variation of the image data-set from the comparative data-set(s), to thereby provide an indication of the presence and/or severity of osteoarthritis in the knee and/or the risk of the knee developing osteoarthritis.

According to another aspect of the present invention there is provided a computer readable medium containing a computer program as defined above.

Again, in these aspects of the invention, the ASM may be configured to identify a set of regions defined by said landmark points on the image, to generate data representative of the image intensity in each said region and include said data in the image data set. In this case, the ASM may be described as an Active Appearance Model (AAM).

Embodiments of the present invention will now be described with reference to the accompanying drawings in which.

Active Shape Modelling is an image processing technique which can be used to analyse shapes which have common features, but which are subject to natural variation.

An Active Shape Model (ASM) is a computer implemented statistical model for matching the shape of an object derived from an image or images of one or more examples of the object. The model comprises a set of landmark points, which are derived from these image(s) and identify predetermined features of the object in question. When applied to a further example of the object in a new image, the model iteratively deforms in accordance with pre-established rules to fit the example of the object in the new image. This is achieved by repeatedly searching the region surrounding each landmark point for features in the image which indicate a better location for the point, and then updating the model parameters to match the new positions, until an optimum fit to the example in the new image is found. The shape of the example in the new image can then be characterised in terms of independent modes of variation from the original shape of the model.

ASMs can thus be used to quantify differences in the shape of a body part between a patient and a control subject.

In the present case, and as discussed in more detail below, the inventors have found that an ASM which covers features of femur and the tibia identifies patterns in the form of these features which have not previously been associated with OA. The inventors have found that the results can be used to indicate incipient osteoarthritis of the knee, or the likelihood of a currently healthy patient developing osteoarthritis in the future, earlier than previously known clinical methods, as well as providing an objective measure of disease severity in terms of a predicted rate of disease progression and/or a predicted rate of progression to surgical intervention.

In a preferred embodiment of the present invention, the apparatus comprises an 85-point ASM which includes landmark points defining the femur, tibia, femoral and tibial osteophytes, tibial plateau, femoral condyles and intercondylar notch.

Figure 1:
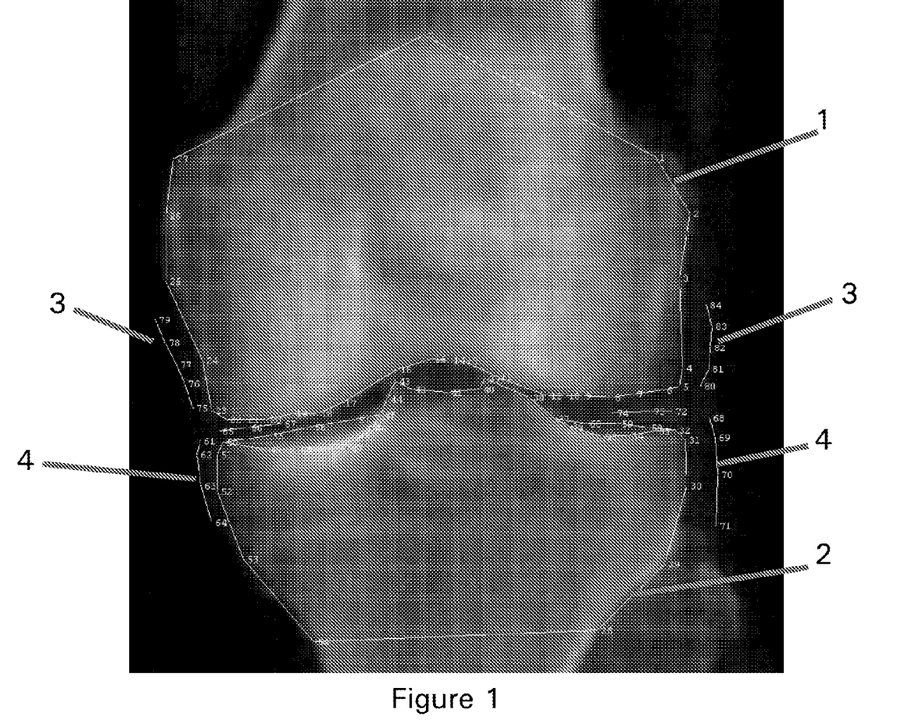
FIG. 1 shows the numbered points of an 85-point ASM used with an embodiment of the present invention.
Figure 2:
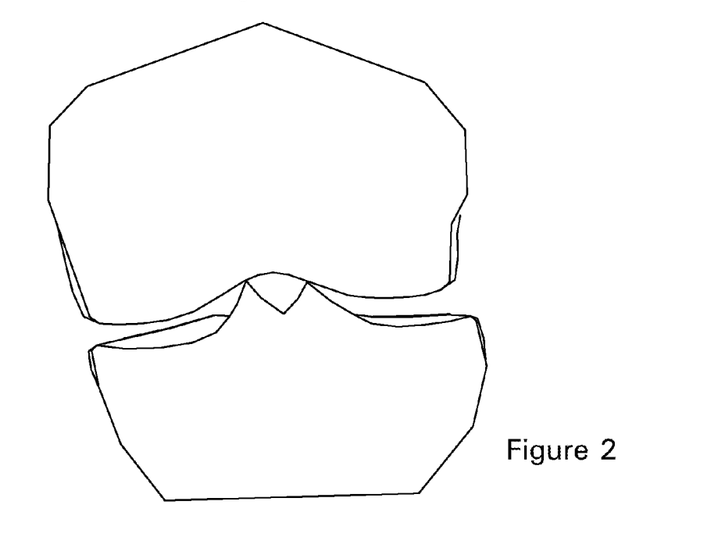
FIG. 2 shows the outline of the mean knee shape obtained by application of the 85 point ASM to a number of radiographs which were considered in studies conducted to evaluate the present invention.

FIG. 1 shows the numbered points of the ASM, as applied to a radiographic image of the knee. The points used to define the osteophytes are shown in exploded view for clarity. The parts of the model which correspond to the femur and the tibia are respectively identified as 1 and 2 in the figure. The parts which correspond to the femoral and tibial osteophytes are respectively identified as 3 and 4. FIG. 2 shows the outline of the mean knee shape from a number of radiographs which were considered in studies conducted to evaluate the present invention.

The ASM is created using an active shape modelling toolkit (ASMTk) (Visual Automation Limited, Manchester, UK), a software program which runs within the MATLAB (The MathWorks Inc, Natick, USA) software environment.

To build the ASM, a set of, for example, 20 radiographic images of the knee are randomly selected to form a training set. The 85 landmark points are identified by an operator on each training image.

Anatomical or key points are placed at anatomical features that can be reproducibly identified on images of the knee, whilst the remaining points (secondary landmarks) are spaced at appropriate positions between these key points.

The software then automatically establishes a set of rules for varying the location of the landmark points to establish the optimum coordinates in a new image. In particular, the system learns to look for specific graphical features, such as hard edges or regions of relative brightness, or features having a specific form in relation to the location of each point. This can be achieved, for example, by means of the Point Distribution Model (PDM).

The apparatus further comprises a database of comparative data. The database is compiled by applying the trained ASM to a set of images taken from control subjects selected as having a healthy knee (ie, experiencing no symptoms of osteoarthritis in the knee) and osteoarthritic subjects. This ensures that the true variation observed in both healthy and diseased knees is included in the database and therefore encompassed within the model. The ASM iteratively deforms in accordance with the aforementioned rules to automatically determine the location of the 85 landmark points for each of the control images.

As part of this process, the software aligns the shapes in the control images by scaling, rotating and translating them in order to minimise the variance, in distance, between equivalent points. This process means that all data about the shape is stored proportionally, rather than absolutely, and the effects of the overall size of the joint on measurements are eliminated.

The co-ordinates of each landmark point for each control image is then stored in the database, together with the mean value and standard deviation for each point.

The apparatus further comprises means for receiving a digital image file containing a radiographic image of the knee region for a patient.

The radiographic image of the patient's knee is obtained using known x-ray photography means. If the image is not already in digital format, it is then scanned, or otherwise converted into a digital file, and supplied to the apparatus. The 85-point ASM is then applied to the radiographic image. The ASM iteratively deforms in accordance with the aforementioned rules to automatically determine the location of the 85 landmark points on the image of the patient's knee.

Once the model has deformed to conform to the shape of the patient's knee, or as part of this process, the software aligns the shapes by scaling, rotating and translating them in order to minimise the variance, in distance, between equivalent points, such that the data is stored proportionally, rather than absolutely, and the effects of the overall size of the joint on measurements are eliminated. The apparatus then records the final coordinates of the landmark points to establish a data-set which characterises the morphometry of the knee. This data set is then compared with the comparative data stored in the database to, for example, determine the variation of the landmark points from the mean values recorded therein.

Principal Component Analysis is used to characterise the shape variation in terms of independent modes of variation. These have been found to be indicative of incipient osteoarthritis, the severity of the disease, and/or the likelihood of developing the disease at some time in the future. Specifically, the image is scored in terms of standard deviations of each mode from the mean for that mode.

Each mode of variation is a linear combination of the original variables (viz. the x and y co-ordinates of each landmark point) and is selected so as to be orthogonal, and therefore linearly independent, of all the other modes. When combined, the modes of variation account for 100% of the variance in the original data set, and every point contributes to a variable extent, to each mode. Each mode is ordered according to the amount of variation explained. Thus, lower numbered modes account for the largest percentage of variance, whilst higher numbered modes explain little variance and can be treated as noise.

The present invention has been described above in terms of an 85 point ASM. However, different numbers of points may be used.

This is the first ASM encompassing the whole knee joint to investigate osteoarthritis. In developing the ASM, the inventors have analysed images of the knee taken for healthy subjects and those suffering from osteoarthritis at various stages. Images have been obtained for a number of subjects at regular intervals over a period of a year. The presence and severity of OA for each image has then been determined by scoring the scans using KL grade. The results show clear relationships between the shape of the knee joint and osteoarthritis severity. Some modes do not correlate with KL grade and yet are related to the presence and/or severity of OA in terms of rate of disease progression. These modes thus identify patterns of features or subtle variations in the overall joint shape which can be used to quantify the presence and/or severity of OA, and which have not previously been recognised as relevant to the presence and/or severity of OA.

More specifically, the modes identify variations in osteophytes, joint space narrowing and the size and shape of the femoral condyles and tibial plateaux, and can distinguish between their unilateral, medial or tibial occurrence.

The majority of shape modes were negatively correlated with KL grade. Mode 1, which accounts for the largest proportion of variation, showed uniform joint space narrowing in both compartments of the knee and femoral and tibial osteophytes. Low scores from modes 2 and 4 represented a similar osteophyte distribution, but identified medial joint space narrowing and showed other differences in the shapes of the femur and tibia. Modes 3 and 6 showed asymmetrical osteophyte formation. Mode 5 highlighted differences in the size and shape of the medial femoral condyle and tibial plateau traditionally associated with OA severity.

Shape mode scores have been found to show clear relationships between the shape of the tibio-femoral knee joint and the severity of osteoarthritis. Mode scores provide a quantitative measure of disease that reflect the traditional KL scores but also unexpectedly extend these by identifying features that change with disease in a coordinated fashion not previously recognised. In addition, the model places the assessment process onto a continuous numerical scale and has the promise of providing a much more powerful means of assessing disease progression and of identifying early signs of disease from conventional radiographs.

The application of the ASM of the invention to general radiographic images is described above. However, the principles of the present invention may equally be applied with other types of image. For example, an ultrasound, Computed Tomography (CT) or MRI image. In particular, the ASM may be applied to images obtained through Dual X-ray Absorptiometry (DXA) scans. DXA scans use two energies of x-ray beams to calculate Bone Mineral Density (BMD). Modern DXA scanners acquire high resolution images allowing possible visualisation of traditional radiographic osteoarthritis features including joint space narrowing and osteophytes, in addition to BMD, whilst exposing the patient to a much lower radiation dose.

The present inventors have established that DXA images can be used to grade severity of osteoarthritis using a standard radiographic scoring method, the Kellgren Lawrence (KL) system, and that the relationship between the shape of the knee and the severity of osteoarthritis observed in radiographs is also found with DXA images using the ASM of the present invention.

In another preferred embodiment of the present invention, the ASM is an Active Appearance Model (AAM).

An AAM is a computer implemented algorithm for matching a statistical model of object shape and appearance to another example of the object in a new image. The term "appearance" in this context refers to the variation of image intensity or texture of the object in the image. In this respect, an AAM uses an ASM to define a region of interest, and then analyses the variation of image intensity within that region. The shape and appearance of the example in the new image can then be characterised in terms of linearly independent modes of variation from the original shape and appearance of the model. AAMs can thus be used to quantify differences in the shape and appearance of a body part between a patient and a control subject.

An AAM is built in the same way as an ASM, using a set of landmark points to describe the outline of one or more features of the object as it appears in an image. In addition to describing the shape, the landmark points are used to segment each feature into a set of triangular regions, with a landmark point at each vertex of each triangle. Appearance (or texture) modes of variation, which quantify the distribution and intensity of the pixels within each region can then be calculated as well as shape modes of variation using Principal Component Analysis. Linear combinations of the shape and appearance modes of variation may then be determined.

Although AAMs may be applied to radiographs, the inventors have established that it is preferable to use images generated from DXA scan data, as the image intensity is standardised in such images. Although DXA images have lower resolution than radiographs, they are acquired using a lower radiation dose and have the added advantage that the image intensity reflects bone mineral density (BMD), such that an AAM applied to a DXA image can describe not only features of the shape of the knee joint, but also the internal spatial distribution of BMD. An AAM applied to a DXA scan thus include data representative of the distribution and variation in BMD within the shape as a series of linearly independent mode scores.

In the present embodiment, the AAM comprises the 85 point ASM shown in FIGS. 1 and 2, which incorporates the outline of the parts of the knee formed by the femur and the tibia, including osteophytes.

To build the AAM, a set of, for example, 20 DXA images of the knee joint are randomly selected to form a training set. The 85 landmark points are identified by an operator on each training image.

A triangulation algorithm, such as the Delauney algorithm, is then applied using the software, to automatically identify triangular regions within the model, whose corners correspond to the landmark points. Of these regions, the specific regions are selected, to ensure that the model covers only areas of bone, and not soft tissue.

The software then automatically establishes a set of rules for varying the location of the landmark points to establish the optimum coordinates. In particular, the system learns to look for specific graphical features, such as hard edges or regions of relative brightness, or features having a specific form in relation to the location of each point, and specific textural features in the triangular regions defined by the location of the landmark points. This can be achieved, for example, by means of the Point Distribution Model (PDM).

The apparatus further comprises a database of comparative data, which is compiled by applying the trained AAM to a set of DXA images taken from control subjects selected as having a healthy knee joint and osteoarthritic subjects. The AAM iteratively deforms in accordance with the aforementioned rules to automatically determine the location of the 85 landmark points, and thus the location of the corresponding triangular regions for each of the control images.

As part of this process, the software aligns the shapes in the control images by scaling, rotating and translating them in order to minimise the variance, in distance, between equivalent points. This process means that all data about the shape is stored proportionally, rather than absolutely, and the effects of the overall size of the joint on measurements are eliminated.

The coordinates of each landmark point for each control image is then stored in the database, together with the mean value and standard deviation for each point. The image intensity within each of the triangular regions is also stored in the database, together with the mean value and standard deviation for each region.

The apparatus further comprises means for receiving a digital image file containing a DXA image of the knee region for a patient. The DXA image of the patient's knee is obtained using known DXA imaging means, such as the GE Lunar iDXA scanner, and supplied as a digital file to the apparatus. The AAM is then applied to the DXA image. The AAM iteratively deforms in accordance with the afornentioned rules to automatically determine the location of the 85 landmark points and the corresponding triangular regions on the image of the patient's knee.

Once the model has deformed to conform to the shape of the patient's knee region, or as part of this process, the software aligns the shapes by scaling, rotating and translating them in order to minimise the variance, in distance, between equivalent points, such that the data is stored proportionally, rather than absolutely, and the effects of the overall size of the joint on measurements are eliminated. The apparatus then records the final coordinates of the landmark points, and the variation of image intensity within the triangular regions of the image, to establish a data-set which characterises the shape and appearance of the knee joint. This data set is then compared with the comparative data stored in the database to, for example, determine the variation of the landmark points from the mean values recorded therein.

Principal Component Analysis is used to characterise the shape and image intensity variation in terms of independent modes of variation. Specifically, the image is scored in terms of standard deviations of each mode from the mean for that mode.

The shape and appearance of the body part may be characterised in terms of shape modes of variation, appearance modes of variation, or a linear combination of both.

Each mode of variation is a linear combination of the original variables and is selected so as to be orthogonal, and therefore linearly independent, of all the other modes. When combined, the modes of variation account for 100% of the variance in the original data set. Each mode is ordered according to the amount of variation explained. Thus, lower numbered modes account for the largest percentage of variance, whilst higher numbered modes explain little variance and can be treated as noise.

In addition to the aspects of the shape of the knee joint discussed above in relation to the 85 point shape only ASM, the 85 point AAM is able to identify areas of sclerosis in both the acetabulum and the femoral head.

DXA imaging enables AAMs to be developed that assess not only the shape or outline of the joint but also the internal bone mineral density, and thus the trabecular structure or "texture" within the region covered by the model. On this basis, the present inventors have developed an 85 point AAM encompassing the whole knee joint to investigate OA. The results show clear relationships between the appearance of the femoro-tibial knee joint and osteoarthritis severity. The additive value of using the appearance model is highlighted by the identification of areas of sclerosis and variation in BMD distribution in both the femur and tibia.

Three of the appearance modes obtained with the 85 point AAM were negatively correlated with KL grade. Only two modes (2 and 4) showed extensive osteophytes. Mode 1 showed differences in the shape of the whole knee joint and the associated BMD distribution, but had no clear evidence of classic KL features. The extremes of modes 2 and 3 showed differences in the shape of the tibia as a whole, with a more angular outline being associated with increased KL grade. The intercondylar notch was noticeably shallower in modes 1 and 2 with increased OA severity. Different patterns of joint space narrowing are distinguished between the modes.

In a preferred embodiment of the present invention, the ASM is a nested ASM. That is to say, the ASM comprises a "master ASM" including the total set of landmark points covering the whole knee joint, from which nested sub-models can be automatically extracted.

The present inventors have established that such a nested ASM can provide a standardised method of assessment and enable individual features and correlations between features to be identified. That is to say, each sub-model in the series comprises a sub-set of the points covered by the previous model in the series. For example, the 85 point ASM of FIG. 1 could be the master ASM, with sub-models covering successively smaller sub-sets of these 85 points. Alternatively, the 85 point ASM could be a sub-model of a more complex master ASM.

The nested-ASM provides a simple and effective means for assessing OA and, when employed universally using the same set of points, enables direct comparison between studies using different model designs.

Active Shape Models use sets of points to identify the outline of the bones and landmark points are placed on defined anatomical features. The precision of the model is maximized by using mathematical constraints to ensure precise and even spacing of intermediate points along smooth lines between landmarks, such as over the femoral head. By using the same set of points, differences between studies will be due to differences in study group, rather than inter-observer variation. Large ASM templates allow visualization of the whole knee joint, whilst smaller models highlight variation in selected regions. Nested designs enable measurement of changes in shape, and their association with OA at all these different levels.

The present invention has been described above in terms of a method and apparatus for identifying the presence and/or severity of OA for a particular patient. However, the apparatus may also be used as biomarker for patent stratification and monitoring OA progression in clinical trials of Disease modifying Osteoarthritic Drugs (DMOADs). In this case, images may be taken for a group of selected subjects, which are analysed using the ASM/AAM to generate a data-set for each image. The results for each image may then be compared to the mean results obtained for the group (or a selection of the group) as a whole.

Figure 3A:
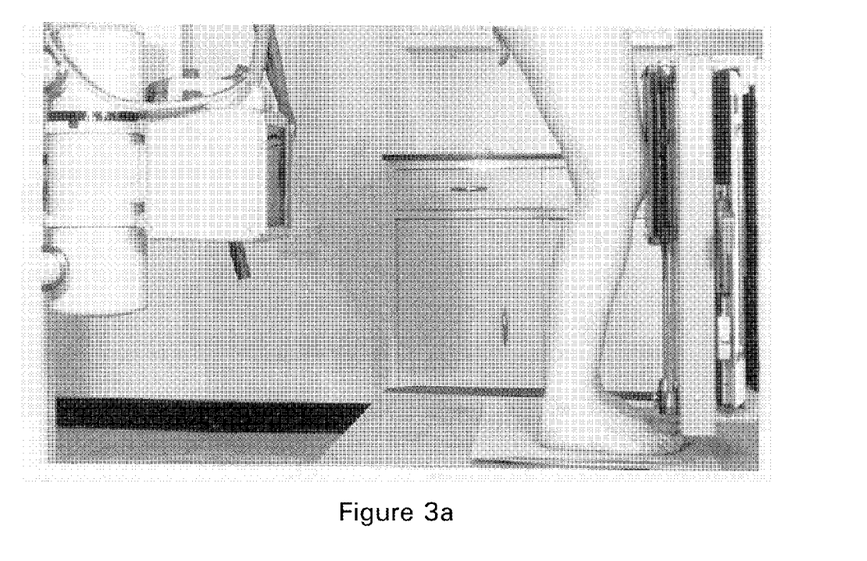
FIGS. 3a and 3b illustrate the taking of radiographic images of the knee.
Figure 3B:
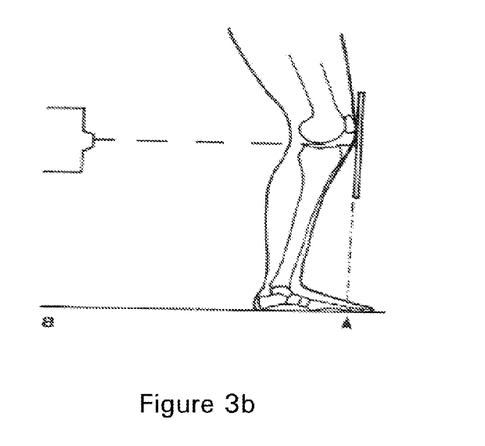

The present invention has been tested using baseline radiographs taken for 107 subjects from the Radiology Department at Aberdeen Royal Infirmary, UK, and affiliated radiology departments. Twelve month radiographs were taken using postero-anterior, weight bearing, semi-flexed metatarsophalangeal (MTP) views, as shown in FIGS. 3a and 3b. The plain radiographs were scored for OA according to the Kellgren Lawrence (KL) scoring system. The cohort encompassed the full spectrum of KL grade (KL=0-4).

In addition, the Grampian NHS Radiology Information System was used to identify patients who had had radiographs of both knees taken in the last 12 months. Baseline Dual X-ray Absorptiometry (DXA) scans were obtained for 107 subjects. 37 were categorised as controls with no radiographic evidence of OA (KL grade 0) in at least one knee. 24 were categorised as having mild OA (KL grade 1 in at least one knee). 22 were categorised as having moderate OA (KL grade of 2 in at least one knee). 24 were categorised as having severe OA (KL grade 3 or 4 in at least one knee).

Of these, 88 subjects attended for follow up scans at 6 and 12 months. 21 were categorised as controls with no radiographic evidence of OA (KL grade 0) in at least one knee. 23 were categorised as having mild OA (KL grade 1 in at least one knee). 21 were categorised as having moderate OA (KL grade of 2 in at least one knee). 23 were categorised as having severe OA (KL grade 3 or 4 in at least one knee).

The DXA scans were obtained by scanning each side separately, with the knee fully extended and positioned as in standard non-weight bearing knee radiographs. A scout scan targeting the femoro-tibial joint space was performed initially in the majority of patients, for optimal positioning of the knee to visualise the tibial spines. Scanning was initiated 4 cm below the apex of the patella.

A random sample of subjects from each of the severity categories (control, mild, moderate and severe, as determined by KL grade) underwent an MRI scan of one knee using a 3 Tesla Achieva MRI Scanner (Philips Medical Systems, Best, Netherlands). The knee to be scanned was the one found to have the higher KL score. The following aspects were assessed:
a) cartilage: sagittal T2-weighted images;
b) delineation of bone and cartilage: sagittal fat suppressed, T1 weighted 3D gradient echo images; and
c) marrow oedema 3D GE fat suppressed T2 weighted images.

The Whole Organ Magnetic Resonance Imaging Score (WORMS) (Peterfy et al, 2004) was used to assess the MRI appearance of the knees. Scoring was performed by a radiology trainee. WORMS assigns a score to knee joint features for increasing severity of OA, including articular cartilage integrity, bone marrow abnormality, cysts, subchondral bone attrition, osteopyhtes, ligaments, meniscus, synovial effusion, loose bodies, synovial cysts and bursitis.

Figure 4:
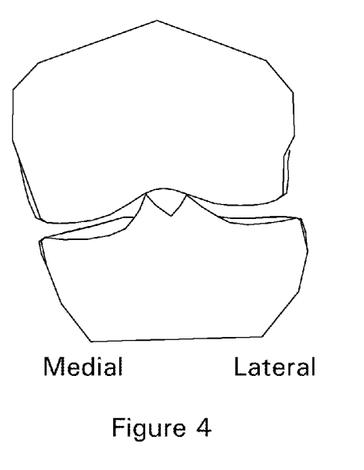
FIG. 4 shows the average knee shape from all the baseline images in a study of the present invention.

The ASM for the knee was applied to all the radiographs from all subjects enrolled in the study. The average knee shape from all the baseline images in the study (both knees) is shown in FIG. 4. The mean shape from the ASM is effectively an outline of a knee with moderate OA. Correlations between each knee shape mode, age and KL grade were assessed to identify modes likely to be of interest for assessing OA progression.

The first 6 out of 15 shape modes were significantly correlated with KL grade, and 5 of these remained significant after Bonferroni correction. Two of the first six modes were also significantly correlated with age (modes 4 and 5) although, after application of the Bonferroni correction for the number of modes compared, only mode 5 remained. In modes 1 to 5, an increase in KL grade was significantly associated with a decrease in mode score. In mode 6, an increase in KL grade was associated with an increase in mode score.

A one way ANOVA (Analysis of Variance), followed by Sidak pot-hoc test, was used to explore further the relationship between KL grade and the first 6 modes. All 6 modes showed an overall significance across the 5 KL grades (Mode 1, 2, 4 and 5 P<0.001, mode 3 P=0.021 and mode 6 P=0.019). The post hoc test identified significant differences in mode scores between different KL grade in mode scores between different KL grade in modes 1, 2, 4 and 5, but not modes 3 and 6.

Osteophyte formation was observed in all 6 modes, and was more pronounced in modes 1 and 2. Uniform joint space narrowing was observed in mode 1 whereas modes 2, 3 and 4 showed unilateral JSN. Variation in the shape of the medial tibial plateau was observed in modes 5 and 6. Similarly, variations in condylar shape were observed in modes 2 and 5.

Mean plots and statistics are given alongside outlines illustrating the range of shapes for selected modes in FIGS. 5a to 5f.

Figure 5A:
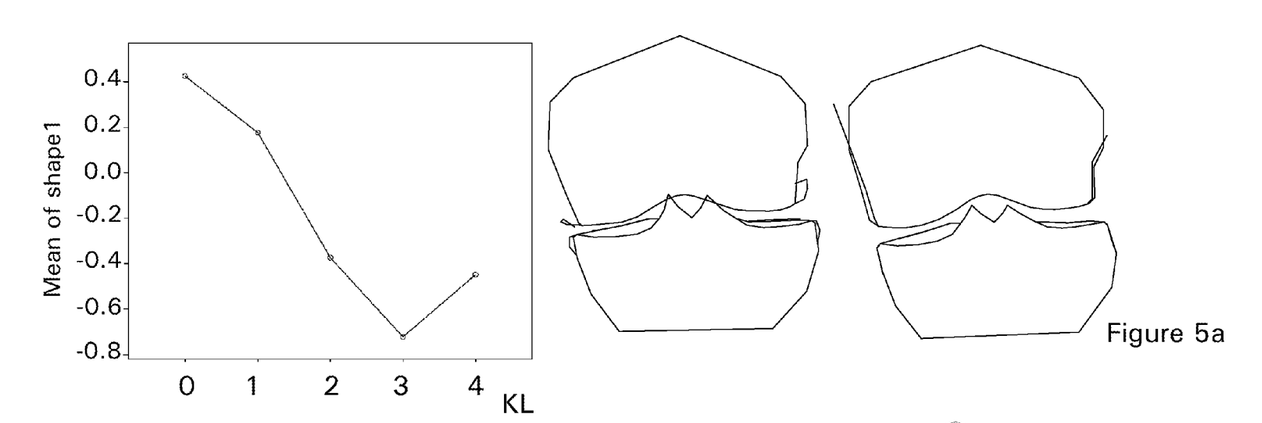
FIGS. 5a to 5f show mean plots and statistics alongside outlines illustrating the range of shapes for selected modes of the 85 point ASM.

FIG. 5a shows a plot of the mean score for shape mode 1 at each KL grade, and line drawings showing the extremes of shape variation (±3 standard deviations). ANOVA P<0.001 and correlation=−0.38 (P<0.001). An increase in KL grade is significantly associated with a decreased mode 1 score. Evidence of femoral and tibial osteophyte formation and uniform joint space narrowing in both compartments is seen. Little evidence of positional change is apparent from the similarity of the tibial plateaux.

Figure 5B:
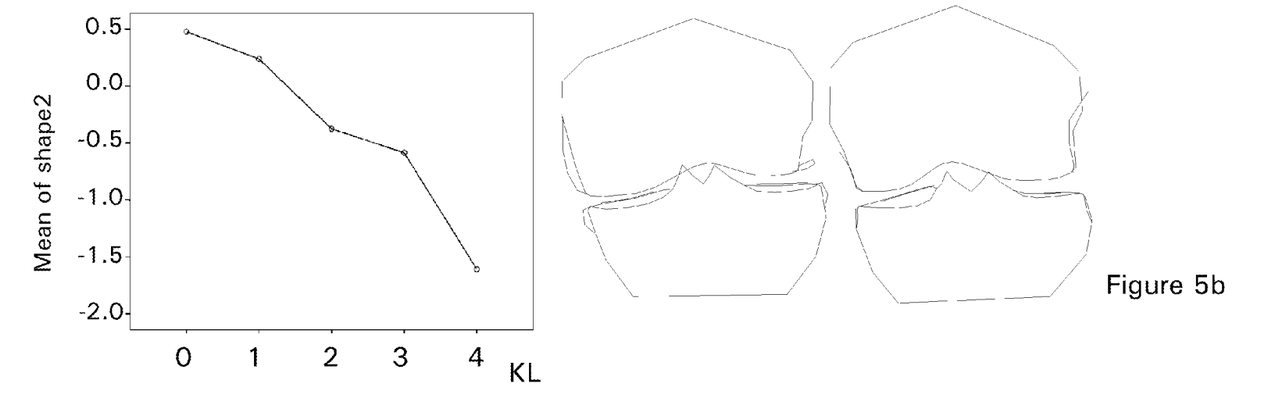

FIG. 5b shows a plot of the mean score for shape mode 2 at each KL grade, and line drawings showing the extremes of shape variation (±3 standard deviations). ANOVA P<0.001 and correlation=−0.48 (P<0.001). An increase in KL grade is significantly associated with a decrease in mode 2 score. Evidence of femoral and tibial osteophyte formation and medial joint space narrowing is seen. The medial femoral condyle also appears flattened and extended.

Figure 5C:
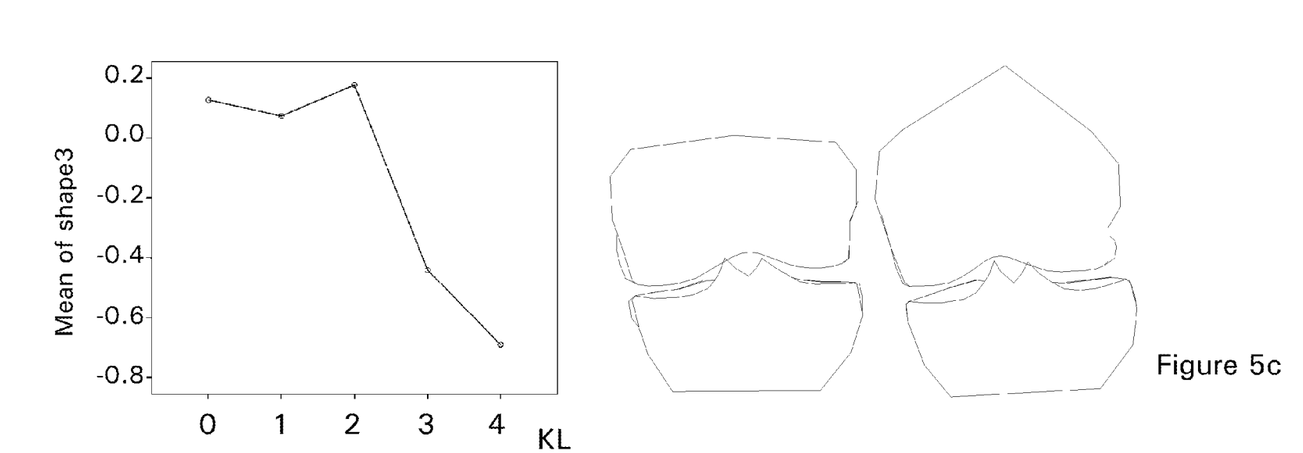

FIG. 5c shows a plot of the mean score for shape mode 3 at each KL grade, and line drawings showing the extremes of shape variation (±3 standard deviations). ANOVA P=0.021 and correlation=−0.17 (P=0.013). Decreased KL grade is significantly associated with decreased mode 3 score. Medial osteophyte formation and joint space narrowing are associated with lows mode scores, whilst lateral osteophyte formation.

Figure 5D:
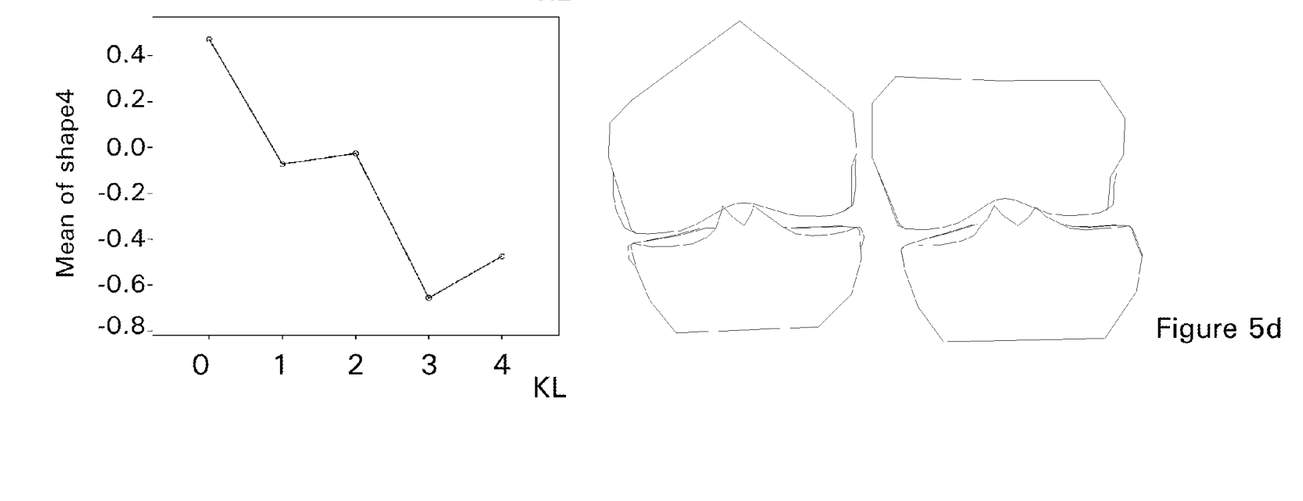

FIG. 5d shows a plot of the mean score for shape mode 4 at each KL grade, and line drawings showing the extremes of shape variation (±3 standard deviations). ANOVA P<0.001 and correlation=−0.31 (P<0.001). An increase in KL grade is significantly associated with a decrease in mode 4 score. Lower mode scores show bilateral osteophyte formation and medial joint space narrowing.

Figure 5E:
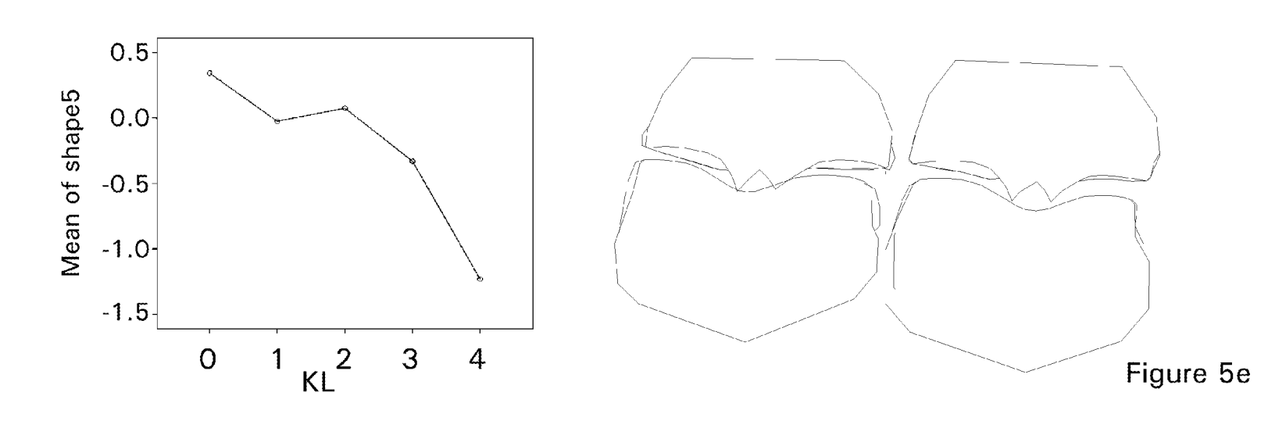

FIG. 5e shows a plot of the mean score for shape mode 5 at each KL grade, and line drawings showing the extremes of shape variation (±3 standard deviations). ANOVA P<0.001 and correlation=−0.28 (P<0.001). An increase in KL grade is significantly associated with a decrease in mode 5 score, some joint space narrowing and unilateral osteophytes. The medial femoral condyle has a wider base and a smoother bone edge and the medial tibial plateau is also wider.

Figure 5F:
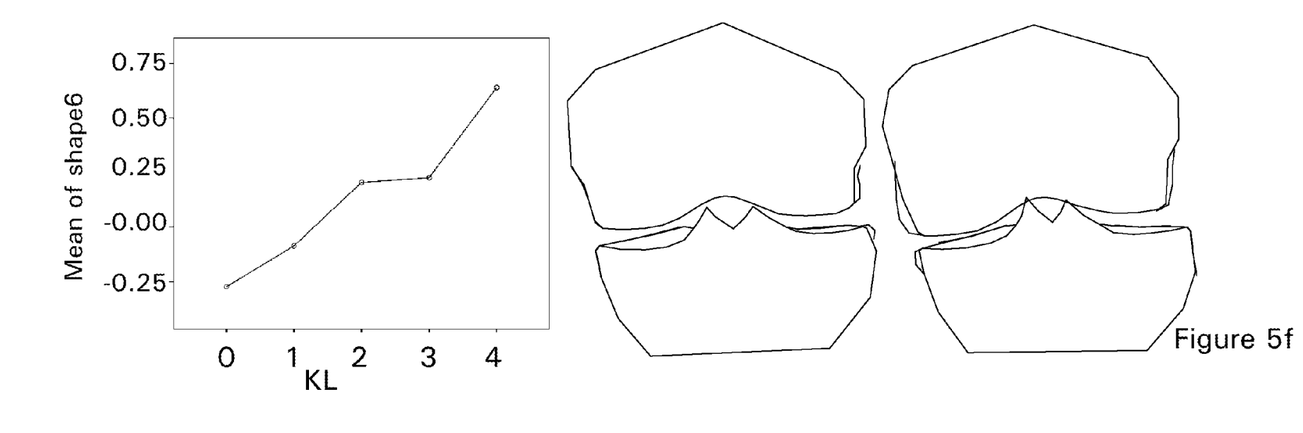

FIG. 5f shows a plot of the mean score for shape mode 6 at each KL grade, and line drawings showing the extremes of shape variation±3 standard deviations). ANOVA P=0.019 Correlation=0.23 (P=0.001). An increase in KL grade is significantly associated with an increase in mode 6 score, medial osteophytes, joint space narrowing, more acute tibial spines and a change in the shape of the medial tibial plateau.

This is the first Active Shape Model encompassing the whole knee joint to investigate OA. The results show clear relationships between the shape of the knee-joint and OA severity. The modes identify variations in osteophytes, joint space narrowing and the size and shape of the condyles and tibial plateaux and can distinguish between their unilateral, medial or tibial occurrence.

The same knee model template was applied to all the DXA images from all individuals enrolled in the study to make an Active Appearance model of the knee joint. The appearance model encompasses changes in external shape and internal "texture" together.

Lower mode scores in mode 1 of the AAM were found to be associated with a shallower intercondylar notch, an extended lateral tibial plateau and medial femoral condyle and a shift in femoral BMD distribution to the lateral side. No evidence of osteophytes was noted.

Lower mode 2 scores showed joint space narrowing, a more uneven distribution of BMD, particularly in the tibia, bilateral osteophytes on both the femur and the tibia, a wider medial femoral condyle and a shallower intercondylar notch. The lateral tibial plateau is extended beyond the lateral femoral condyle, possibly indicating malalignment.

This indicates the additive value of using AAM over (shape only) ASM, since areas of sclerosis and variation in BMD in both the femur and tibia are identified, indicative of anatomical features of OA.

Correlations between each knee-shape mode, age and KL grade were then assessed to identify modes likely to be of interest for assessing OA progression.

Figure 6A:
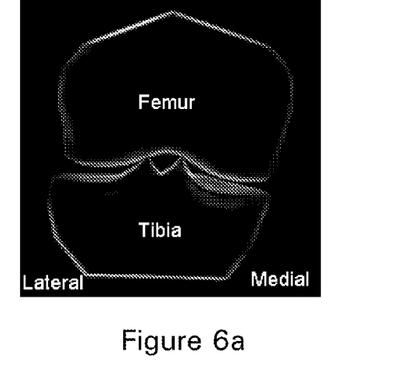
FIG. 6a is a line drawing of the area covered by an 85 point AAM used with an embodiment of the present invention.
Figure 6B:
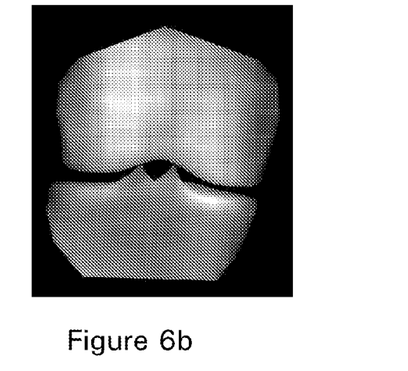
FIG. 6b is a greyscale image of the mean appearance model obtained from baseline iDXA scans of the knee obtained in a study of the present invention.

7 of the first 15 modes were found to be significantly correlated with KL grade. FIG. 6a is a line drawing of the area covered by the AAM, and indicates the medial and lateral sides of the femur and tibia. FIG. 6b is a greyscale image of the mean appearance model obtained from the baseline iDXA scans of the knee.

Following application of the Bonferroni correction, only modes 1 and 4 remained significant (P<0.0033), none of which was significantly associated with age. A one-way ANOVA (Sidak post hoc test) was applied to explore further the first 4 modes of variation. This found significant differences between the KL grade in al 4 modes (P<0.01). Mode 2 had the strongest relationship with KL grade (R=0.68, P<0.001). Post hoc analysis of mode 2 identified significant differences between each pair of KL grades (except 3 and 4).

Mean plots and statistics are given alongside outlines illustrating the range of shapes for selected modes in FIGS. 7a to 7d.

Figure 7A:
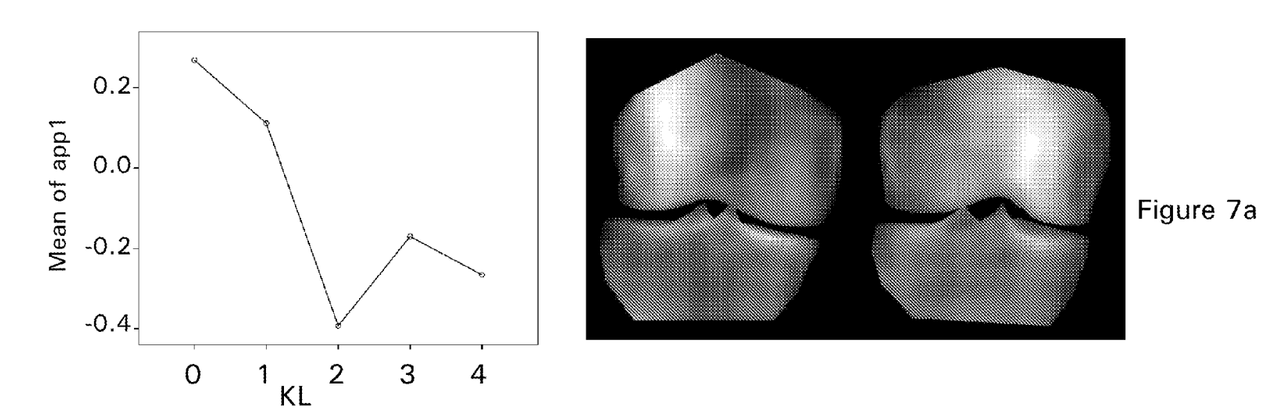
FIGS. 7a to 7d show mean plots and statistics alongside outlines illustrating the range of shapes for selected modes of the 85 point AAM.

FIG. 7a shows a plot of the mean score for appearance mode 1 at each KL grade, alongside a greyscale image showing the extremes of shape variation. ANOVA P=0.01 and correlation=-0.20 (P=0.003). Lower mode scores were generally associated with increasing severity of OA. Lower mode scores corresponded to shallower intercondylar notch, an extended lateral tibial plateau, an extended medial femoral condyle and a shift in femoral BMD distribution to the lateral side. No evidence of osteophytes is noted.

Figure 7B:
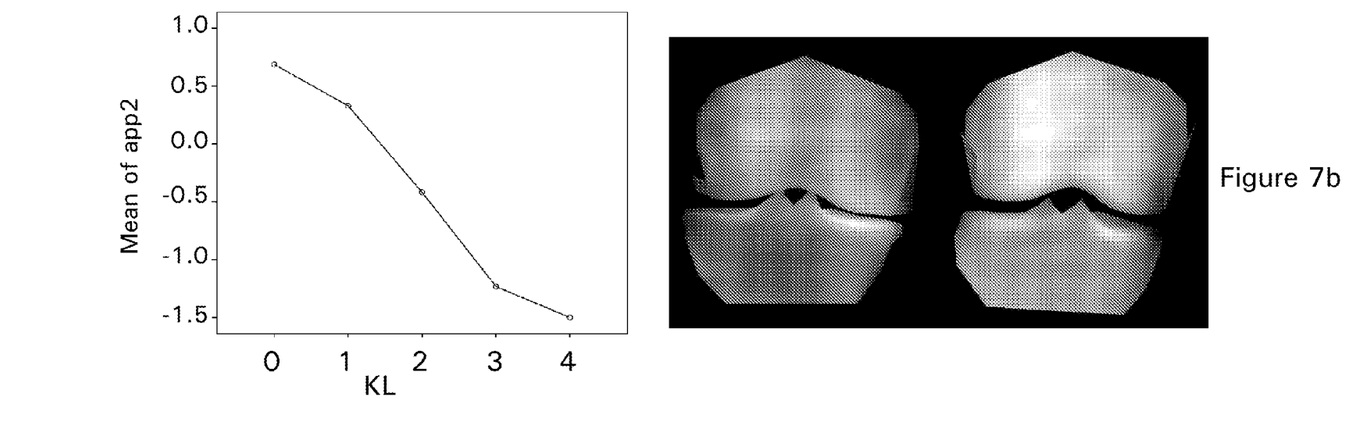

FIG. 7b shows a plot of the mean score for appearance mode 2 at each KL grade, alongside a greyscale image showing the extremes of shape variation. ANOVA P<0.001 and correlation=-0.68 (P<0.001). Low mode 2 scores are associated with increased KL grade, joint space narrowing a more uneven distribution of BMD (particularly in the tibia), bilateral osteophytes on both the femur and tibia, a wider medial femoral condyle, a shallower intercondylar notch. The lateral tibial plateau is extended beyond the lateral femoral condyle, possibly indicating malalignment. The shape of the tibia as a whole is more angular in severe OA.

Figure 7C:
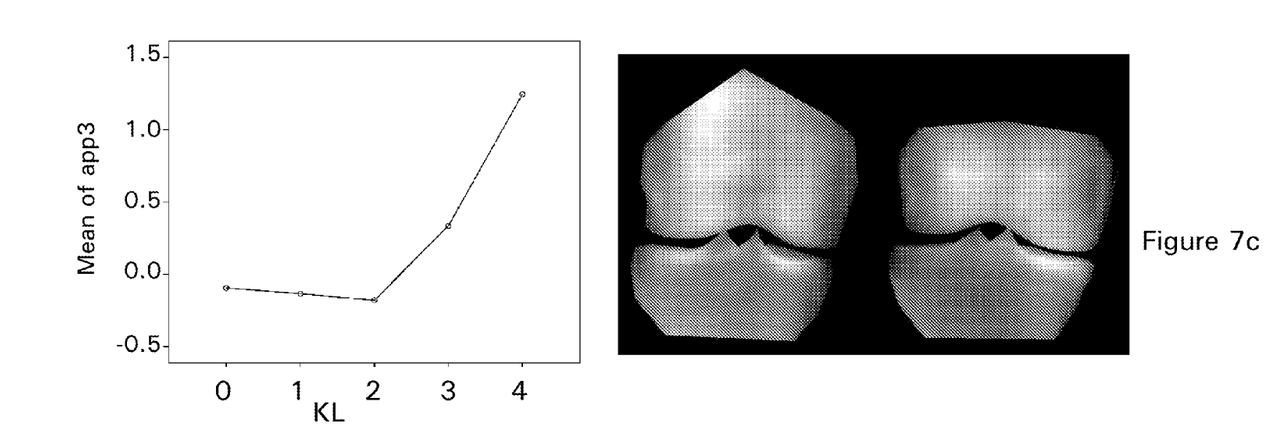

FIG. 7c shows a plot of the mean score for appearance mode 3 at each KL grade, alongside a greyscale image showing the extremes of shape variation. ANOVA P=0.001 and correlation=0.20 (P=0.003). High mode 3 scores are associated with severe OA (KL grades 3 and 4), with evidence of medial joint space narrowing, a more angular tibia with abrupt plateau "corners", the tibial BMD distribution is also skewed to the medial side.

Figure 7D:
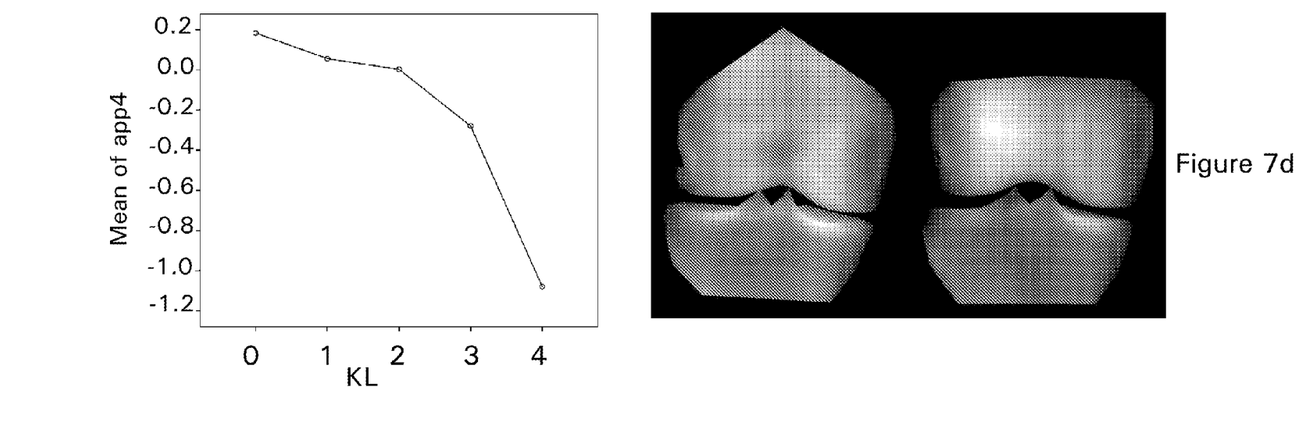

FIG. 7d shows a plot of the mean score for appearance mode 4 at each KL grade, alongside a greyscale image showing the extremes of shape variation. ANOVA P=0.009 and correlation=-0.22 (P=0.002). Low mode 4 scores were associated with increased severity of OA, lateral femoral osteophytes, bilateral joint space narrowing and tibial sclerosis.

This is the first Active Appearance Model encompassing the whole knee joint to investigate osteoarthritis. The results show clear relationships between the appearance of the knee-joint and osteoarthritis severity. The additive value of using the appearance model is highlighted by the identification of areas of sclerosis and variation in BMD distribution in both the femur and tibia.

Figure 8:
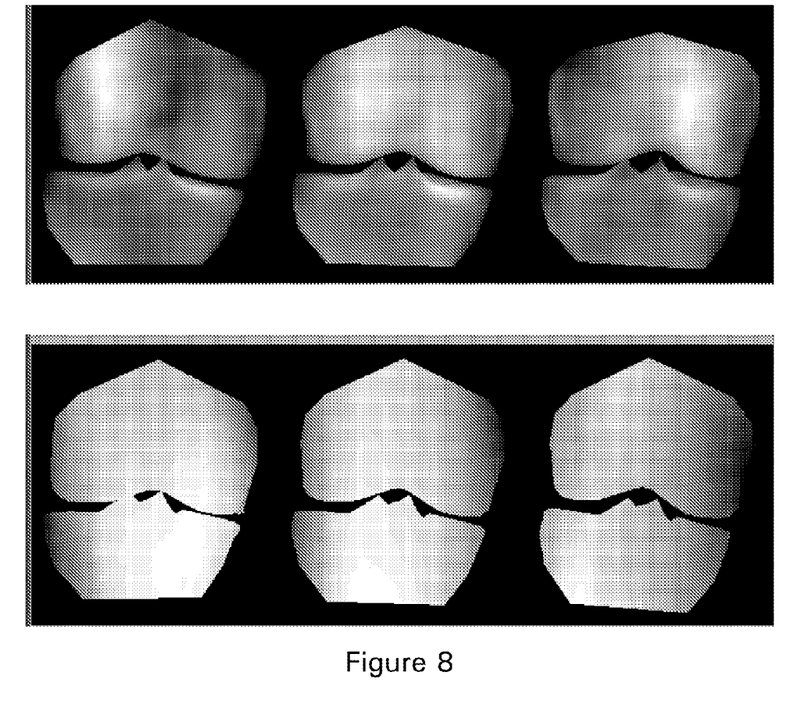
FIG. 8 shows the increased level of detail and variation in greyscale across the femur and tibia in appearance mode 1 in the iDXA images (top row) as compared with that in the radiographs (bottom row).

AAMs of the knee were built using both iDXA and radiograph images of the knee in order to compare the additive value of the AAM compared with the ASM for each imaging modality. FIG. 8 shows the increased level of detail and variation in greyscale across the femur and tibia identified by Appearance mode 1 in the iDXA images (top row) compared with that in the radiographs (bottom row). The increased standardisation available from the iDXA images is reflected by an increased level of detail available from the iDXA model, compared to the diffuse appearance of the radiograph model.

As many of the mode scores were significantly correlated with KL grade, stepwise linear discriminant analysis (LDA) was used to determine whether a combination of the shape (first 6 modes) and appearance (first 4 modes) could correctly identify the KL grade.

Stepwise LDA automatically selected appearance mode 2 and shape modes 1, 5 and 4 respectively using forward stepwise selection. Classification accuracy was calculated using both the original calculated classification results and using Leave-one-out cross validation.

The similarity between the predicted KL grade from the AAM and the KL grade assigned by a trained rheumatologist was calculated using Quadratic Weighted Kappa (QWK). The 'original' predicted membership had a QWK of 0.77, whilst the predicted membership calculated from the cross-validated analysis had a QWK of 0.74. These results show that the AAM could classify knees from the same set of iDXA images with the same accuracy as humans (0.66-0.85).

The first 15 shape modes were used as input to a forward stepwise linear discriminant analysis (LDA), and the KL grade used as output. This was then repeated for the first 15 appearance modes and all 30 (15 shape, 15 appearance) modes together. Results from the stepwise LDA were assessed using leave-one-out cross validation to avoid overestimation of the accuracy of the classifier. The level of agreement with the KL grade was calculated using quadratic rated kappa.

Forward stepwise linear discriminant analysis selected 9, 9 and 8 modes respectively from the knee shape, appearance and combined datasets. When both shape and appearance modes were available to the classifier, the first mode selected (that which on its own can best separate the KL grades) was an appearance mode. The strongest classifier was found using the combination of shape and appearance and the weakest classifier used shape modes alone.

Shape modes 2 5 and 6 and appearance modes 2, 4 and 7 were selected for comparison with the MRI data. Pearson's correlation was used to test for differences in the MRI scans that are related to the shape and appearance mode scores. These mode scores were compared to the overall scores for cysts, bone marrow lesions (oedema), osteophytes, femoral head flattening and cartilage thickness. Medial compartment, lateral compartment and total scores were selected from the WORMS scoring system, patella-femoral compartment data was ignored as it would not correspond directly to Antero-posterior iDXA scans.

Both shape mode 2 and appearance mode 2 were significantly correlated with all the WORMS scores listed ($P<0.05$). Shape modes 5 and 6 were correlated with all features ($P<0.05$) except bone marrow lesions and cysts. Appearance mode 4 was correlated with all features except lateral cartilage thickness ($P<0.05$) and appearance mode 7 was not correlated to any of the WORMS features, despite having a significant correlation with KL grade.

The invention claimed is:

1. Apparatus for analysing the morphometry of a human knee joint, the apparatus comprising:
    image receiving means for receiving a digital image of a knee joint;
    image analysis means comprising a master-ASM (Active Shape Model) configured to identify a set of landmark points on said image, and one or more sub-ASMs configured to identify a subset of the landmark points the master-ASM is configured to identify, wherein said set of landmark points includes points which define regions of the knee formed by the femur and the tibia, the ASMs being further configured to generate an image data-set from the co-ordinates of said landmark points; and
    data comparison means for comparing said image data-set with one or more comparative data-sets to thereby obtain value(s) for one or more output modes which characterise the variation of the image data-set from the comparative data-set(s), to thereby provide an indication of the presence and/or severity of osteoarthritis in the knee and/or the risk of the knee joint developing osteoarthritis.

2. Apparatus as claimed in claim 1 wherein the ASMs are configured to identify landmark points defining femoral osteophytes.

3. Apparatus as claimed in claim 1 wherein the ASMs are configured to identify landmark points defining tibial osteophytes.

4. Apparatus as claimed in claim 1 wherein the ASMs are configured to identify landmark points defining the tibial plateau.

5. Apparatus as claimed in claim 1 wherein the ASMs are configured to identify landmark points defining the femoral condyles.

6. Apparatus as claimed in claim 1 wherein the ASMs are configured to identify landmark points defining the inter-condylar notch.

7. Apparatus as claimed in claim 1 wherein the ASMs are further configured to identify a set of regions defined by said landmark points on the image, to generate data representative of the image intensity in each said region and include said data in the image data set.

8. Apparatus as claimed in claim 7 wherein the ASMs are Active Appearance Models (AAMs).

9. Apparatus according to claim 1 wherein the data comparison means is configured to apply Principal Component Analysis to characterise the variation of the image data-set from the comparative data-sets in terms of independent modes of variation.

10. Apparatus according to claim 9, comprising a series of one or more sub-ASMs, the first being configured to identify a subset of the landmark points the master-ASM is configured to identify, and the further sub-ASM(s) each being configured to identify a subset of the landmark points identified by the previous sub-ASM in the series.

11. Apparatus according to claim 1 wherein the data comparison means compares the image data set with the comparative data sets by examining how the location of landmark points deviates from the mean co-ordinates of the comparative data-set(s).

12. Apparatus according to claim 1 wherein the digital image of the knee joint is obtained from one of a radiographic image, a Dual X-ray Absorptiometry (DXA) image, an ultrasound image, a Magnetic Resonance Image (MRI), and a Computed Tomography (CT) image thereof.

13. A method for analysing the morphometry of a human knee joint, the method comprising:
    providing a digital image of a knee joint;
    applying to said image a masterASM (Active Shape Model) configured to identify landmark points on said image, and one or more sub-ASMs configured to identify a subset of the landmark points the master-ASM is configured to identify, wherein said set of landmark points includes points which define regions of the knee formed by the femur and the tibia,
    generating an image data-set from the co-ordinates of said landmark points; and
    comparing said image data-set with one or more comparative data-sets to thereby obtain at least one value for one or more output modes which characterize the variation of the image data-set from the one or more comparative data-sets.

14. A non-transitory computer-readable medium storing a computer program for analysing the morphometry of a human knee joint, the program comprising:
    image receiving code for receiving a digital image of a knee joint;
    image analysis code comprising Active Shape Model (ASM) code including code for a master-ASM (Active Shape Model) configured to identify a set of landmark points on said image, and code for one or more sub-ASMs configured to identify a subset of the landmark points the master-ASM is configured to identify, wherein said set of landmark points includes points which define regions of the knee formed by the femur and the tibia, the ASM code being further configured to generate and store an image data-set from the co-ordinates of said landmark points; and
    data comparison code configured to compare said image data-set with one or more comparative data-sets to thereby obtain value(s) for one or more output modes which characterise the variation of the image data-set from the comparative data-set(s), to thereby provide an indication of the presence and/or severity of osteoarthritis in the knee and/or the risk of the knee joint developing osteoarthritis.

* * * * *